US008483486B1

(12) United States Patent
Pinkus et al.

(10) Patent No.: US 8,483,486 B1
(45) Date of Patent: Jul. 9, 2013

(54) AUTOMATIC LANDOLT C GAP DETECTION SOFTWARE ARCHITECTURE FOR IMAGE QUALITY ANALYSIS

(75) Inventors: Alan R. Pinkus, Bellbrook, OH (US); David W. Dommett, Beavercreek, OH (US); Harry Lee Task, Tucson, AZ (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 317 days.

(21) Appl. No.: 13/025,624

(22) Filed: Feb. 11, 2011

(51) Int. Cl.
*G06K 9/46* (2006.01)
(52) U.S. Cl.
USPC ............ 382/194; 382/100; 382/181; 382/299
(58) Field of Classification Search
USPC .................. 382/100, 181, 194, 299
See application file for complete search history.

(56) References Cited

U.S. PATENT DOCUMENTS

| | | | | |
|---|---|---|---|---|
| 4,607,923 A * | 8/1986 | Task et al. | ...................... | 351/239 |
| 4,615,594 A * | 10/1986 | Task | .............. | 351/239 |
| 4,618,231 A * | 10/1986 | Genco et al. | .................. | 351/237 |
| 5,880,814 A * | 3/1999 | McKnight et al. | ............. | 351/239 |
| 7,537,343 B2 * | 5/2009 | Kanazawa et al. | ............ | 351/239 |
| 7,771,051 B2 * | 8/2010 | Hirji | ............................ | 351/223 |
| 7,819,524 B2 * | 10/2010 | Kanazawa et al. | ............ | 351/201 |
| 8,083,353 B2 * | 12/2011 | Hytowitz | ...................... | 351/239 |
| 8,184,923 B2 * | 5/2012 | Hayakawa et al. | ............ | 382/267 |
| 8,197,065 B2 * | 6/2012 | Yoo et al. | ...................... | 351/203 |
| 8,324,564 B1 * | 12/2012 | Pinkus et al. | .............. | 250/252.1 |

OTHER PUBLICATIONS

Reproducibility—Landolt C's, Pinkus et al., SAFE journal—30(1), 2000, pp. 1-6.*
Capturing the sample—model, Hogervorst, M.A et al., SPIE proceedings vol. 4372, 2001, pp. 62-73.*
Quad-Emissive—Analyses, Pinkus et al., SPIE, vol. 7336-50, 2009, pp. 1-10.*
Pinkus, A. R., et al., "Quad-Emissive Display for Multi-spectral Sensor Analyses.", Proceedings of SPIE, Orlando, FL, vol. 7336-50 (2009).
Task, H. L., et al., "Theoretical and Applied aspects of night vision goggle resolution and visual acuity assessment.", Helmet- and Helmet-Mounted Displays: Technologies & Applications, Proceedings of SPIE, Orlando, FL, vol. 6557, 65570P-1-11 (2007).
Pinkus, A. R., et al., "Reproducibility Limits of Night Vision Goggle Visual Acuity Measurements", SAFE Journal, 30(1) (2000).
Pinkus, A. R., et al., "Measuring observers' visual acuity through night vision goggles.", SAFE Symposium Proceedings 1998, 36th Annual Symposium, pp. 1-11 (1998).

(Continued)

*Primary Examiner* — Jayesh A Patel
(74) *Attorney, Agent, or Firm* — AFMCLO/JAZ; Charles Figer

(57) ABSTRACT

A method, apparatus and program product are presented for determining an orientation of a Landold C in an image containing a plurality of pixels. A center of the Landolt C is determined. A plurality of rays is extended from the center of the Landolt C radially outward. A plurality of distances is determined, where each distance of the plurality of distances represents a distance from the center of the Landolt C to a darkest pixel along each ray of the plurality of rays. A peak in the plurality of distances is identified. And the orientation of the Landolt C is determined based on the peak in the plurality of distances.

20 Claims, 17 Drawing Sheets

OTHER PUBLICATIONS

Bijl, P., et al., "A critical evalutaion of test patterns for EO system characterization.", SPIE Proceedings vol. 4372, pp. 27-38 (2001).

Hogervorst, M. A., et al., "Capturing the sampling effects: a TOD sensor performance model.", SPIE Proceedings vol. 4372, pp. 62-73 (2001).

McHugh, S. W., et al., "TOD test method for characterizing electro-optical system performance.", SPIE Proceedings vol. 4372, pp. 39-45 (2001).

Bailey, I., et al., "New design principles for visual acuity letter charts.", American Journal of Optometry and Physiological Optics, 53, pp. 740-745 (1976).

Brown, R., et al., "New directions in psychology I", pp. 89-155, New York, Rinehart and Winston (1962).

Farrell, R., et al., "Design handbook for imagery interpretation equipment.", pp. 3.1-9-3.1-18, 4.3-60-4.3-61, 8.0-17-8.0-18, Seattle, Boeing Aerospace Company (1984).

Bijl, P., et al., "Guidelines for Accurate TOD Measurement.", SPIE Proceedings, vol. 3701, pp. 14-25 (1999).

Military Specification MIL-L-85762A, "Night vision imaging system (NVIS) compatible interior aircraft lighting." (Jan. 24, 1986).

Miller, R., et al., "Comparative visual performance with ANVIS and AN/PVS-5A night vision goggles under starlight conditions.", Technical Report No. USAFSAM-TR-84-28, USAF School of Aerospace Medicine, Brooks AFB, TX (1984).

National Academy of Sciences, "Recommended standard procedures for the clinical measurement and specification of visual acuity.", Report of Working Group 39, Committee on Vision, Advances in Ophthalmology, 41, pp. 103-148 (1980).

Pinkus, A. R., et al., "The effects of aircraft transparencies on night vision goggle-mediated visual acuity.", SAFE Symposium Proceedings 1997, 35th Annual Symposium Sep. 8-10, pp. 93-104 (1997).

Simpson, W. A., "The Step method: A new adaptive psychophysical procedure.", Perception & Psychophysics, 45(6), pp. 572-576 (1989).

Stefanik, R., "Image intensifier system resolution based on laboratory measured parameters.", Technical Report No. 0112, Night Vision and Electronic Sensors Directorate, Ft. Belvoir, VA (Aug. 1994).

Task, H. L., "An evaluation and comparison of several measures of image quality for television displays.", Technical Report No. AMRL-TR-79-7, NTIS, Alexandria, VA (1979).

Wiley, R., "Visual acuity and stereopsis with night vision goggles.", Technical Report No. USAARL 89-9, U.S. Army Aeromedical Research Laboratory, Ft. Rucker, AL (1989).

Bijl, P., "TOD Predicts Target Acquisition Performance for Staring and Scanning Thermal Images.", SPIE Proceedings, vol. 4030, pp. 96-103 (2000).

* cited by examiner

| Ray Number | Distance in Pixels |
|---|---|
| 58 | 7 |
| 60 | 9 |
| 62 | 9 |
| 64 | 7 |
| 66 | 9 |
| 68 | 10 |
| 70 | 14 |
| 72 | 9 |
| 74 | 8 |
| 76 | 6 |
| 78 | 7 |
| 80 | 7 |
| 58 | 7 |

| Distance | IR | NIR | VIS |
|---|---|---|---|
| 5.3 m | 100 | 100 | 100 |
| 7.1 m | 100 | 100 | 100 |
| 9.5 m | 100 | 100 | 100 |
| 12.5 m | 100 | 75 | 100 |
| 16.9 m | 75 | 50 | 50 |
| 22.5 m | 25 | 25 | 0 |
| 30.0 m | 50 | 0 | 0 |
| 40.0 m | 50 | 0 | 0 |

150 ⟵ (table)

152　154　156　158

AUTOMATIC LANDOLT C GAP DETECTION SOFTWARE ARCHITECTURE FOR IMAGE QUALITY ANALYSIS

RIGHTS OF THE GOVERNMENT

The invention described herein may be manufactured and used by or for the Government of the United States for all governmental purposes without the payment of any royalty.

CROSS-REFERENCE TO RELATED APPLICATIONS

This application is related to U.S. patent application Ser. No. 13/025,570, filed on even date herewith by Pinkus et al., and entitled "Automatic Triangle Orientation Detection Algorithm" (AFD 1161), the disclosure of which is incorporated by reference herein in its entirety.

BACKGROUND OF THE INVENTION

The present invention relates to pattern and object recognition, and more particularly to a method for detecting an object in a digital image.

Over the years, there have been many methods developed to determine the image quality of an image-generating system such as a sensor/display combination. In most cases, the final consumer of the image produced is a human observer using their visual capability to extract visual information from the displayed image. In recent years, imaging systems and image manipulation have moved from the analog world to the digital world, which has probably added a bit more confusion to the issue of image quality or resolution.

In general, resolution is the ability of a sensor/display system to produce detail; the higher the resolution, the finer the detail that can be displayed. With the advent of digital imagery and sensor detectors that are composed of an array of discrete elements, it is tempting, and not entirely wrong, to characterize the resolution of the system by the number of picture elements (pixels) for the display or sensor elements in the case of the sensor. For example, VGA resolution for a computer display is 480 elements high by 640 elements wide and SVGA is 600×800 elements. This describes the number of samples that can be displayed; however, the number of pixels alone says nothing of the quality of the actual display medium characteristics (luminance, contrast capability, noise, color, refresh rate, active area to total area ratio, etc.) or of the signal/information used to feed the individual pixels. Nevertheless, this numerical value of pixel or sensor element count is often given as a primary metric to the resolution (quality) of the sensor or display.

Another common approach to determining the resolution of a sensor/display system is to image an appropriate resolution test target and determine the smallest sized critical test pattern element that can be seen by a human observer. Many test patterns have been developed over the years such as grating, tri-bars, tumbling Es, the Snellen chart, and the Landolt C chart to test vision or to test imaging systems using vision. The test pattern typically has test elements of various sizes so that the human observer can pick out the smallest size that they can resolve. An alternative to the multi-sized test pattern is to use a single size test element, but image it at various distances until a distance is obtained at which the test object is barely resolved.

Related to resolution is visual acuity, which is acuteness or clearness of vision that is dependent on the sharpness of the retinal focus within the eye and the sensitivity of the interpretative faculty of the brain. For example, numerous methods have been used to determine night vision goggle ("NVG") visual acuity such as limiting resolution, Snellen Acuity, square wave targets, Landolt Cs, adaptive psychophysical, and directly measuring the psychometric function or the "frequency of seeing" curve. Each method produces a number that is composed of an actual acuity value plus error. There can be many sources of error but the largest is generally the method itself as well as the inherent variability of the observer while working under threshold conditions. Observer variability may be reduced through extensive training, testing the same time every day, and shortened sessions in order to reduce eye fatigue. Additionally, even though observers are given specific instructions, response criteria may also vary among or within observers; even over the course of a single experimental session. To assist in eliminating the criteria problem, a four alternative forced-choice paradigm was developed and utilized to measure the entire psychometric function. This paradigm allowed for any desired response criteria level (e.g., 50% or 75% corrected for chance, probability of detection) to be selected for the prediction of (NVG) visual acuity performance. Although all of the preceding was directed at visual acuity/resolution assessment of night vision goggles using multiple human observers the "resolution" concept applies equally well to digital imagery.

Current and future military weapons systems (e.g. micro UAVs, satellites, surveillance, weapons aiming optics, day/night head-mounted devices) will increasingly rely on digitally-based multi-spectral imaging capabilities. With digital media comes the potential to register, fuse, and enhance digital images whether they are individual images or streaming video gathered in real-time. Multi-spectral fusion and enhancement provides the greatly increased potential to detect, track, and identify difficult targets, such as those that are camouflaged, buried, hidden behind a smoke screen or obscured by atmospheric effects (haze, rain, fog, snow).

There are several different conventional techniques to assess the relative improvement in image quality when an image-enhancing algorithm has been applied to a digital image. The testing of enhancing effects often consists of subjective quality assessments or measures of the ability of an automatic target detection program to find a target before and after an image has been enhanced. It is rare to find studies that focus on the human ability to detect a target in an enhanced image using scenarios that are relevant for the particular application for which the enhancement is intended. While a particular algorithm may make an image appear substantially better after enhancement, there is no indication as to whether this improvement is significant enough to improve human visual performance.

Therefore, there is a need in the art to automatically assess image quality in terms of modeled human visual resolution perceptual qualities (i.e., the "frequency of seeing" curve) but without the need to actually use human observers.

SUMMARY OF THE INVENTION

Embodiments of the invention provide a method, apparatus and a program product configured to detect an orientation of a Landold C in an image containing a plurality of pixels. In these embodiments, a center of the Landolt C is determined. A plurality of rays is extended from the center of the Landolt C radially outward to determine a plurality of distances. Each distance of the plurality of distances represents a distance from the center of the Landolt C to a darkest pixel along each ray of the plurality of rays. The plurality of distance data may be arranged to represent a "signal" from which a peak may be identified. The orientation of the Landolt C may then be determined based on the peak in the "signal" representing the plurality of distances.

In some embodiments, the orientation algorithm above may be a semi-automatic procedure where the center of the Landolt C may be determined by using a human observer to select a pixel of the plurality of pixels representing the center of the Landolt C.

In other embodiments, the orientation algorithm above may be a fully automatic procedure where the pixels of the image are organized in rows and columns and the center of the Landolt C may be determined by determining an approximate center of the Landolt C. A plurality of pixels may be binarized within an area defined by a radius surrounding the approximate center, with each binarized pixel of the plurality of pixels being changed to one of either black or white. The leftmost and right most columns of binarized pixels containing a black pixel may then be determined and the uppermost and lowermost rows of binarized pixels containing a black pixel may also be determined. The center of the Landolt C may then be determined from the uppermost and lower most rows and the leftmost and rightmost columns.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Embodiments of the invention address the need in the art by providing a software architecture and procedure that allow automatic detection of digital images and quality using only a computer. This is in contrast to either simple "before" and "after" subjective visual comparisons or laborious and costly psychophysical procedures requiring extensive testing of multiple trained observers who are required to view and correctly judge the different orientation of many differently sized stimuli such as Landolt Cs or triangles. Embodiments of the invention utilize a software-implemented automatic Landolt C Orientation Detection model, which has been designed to produce a similar frequency of seeing function as those produced by real observers. Thus, the variations among different multispectral sensors as well as image registration, fusion, and/or enhancement algorithms can be relatively quickly, accurately, and automatically assessed in terms of human visual perception but without the need for human observers.

Figure 1:
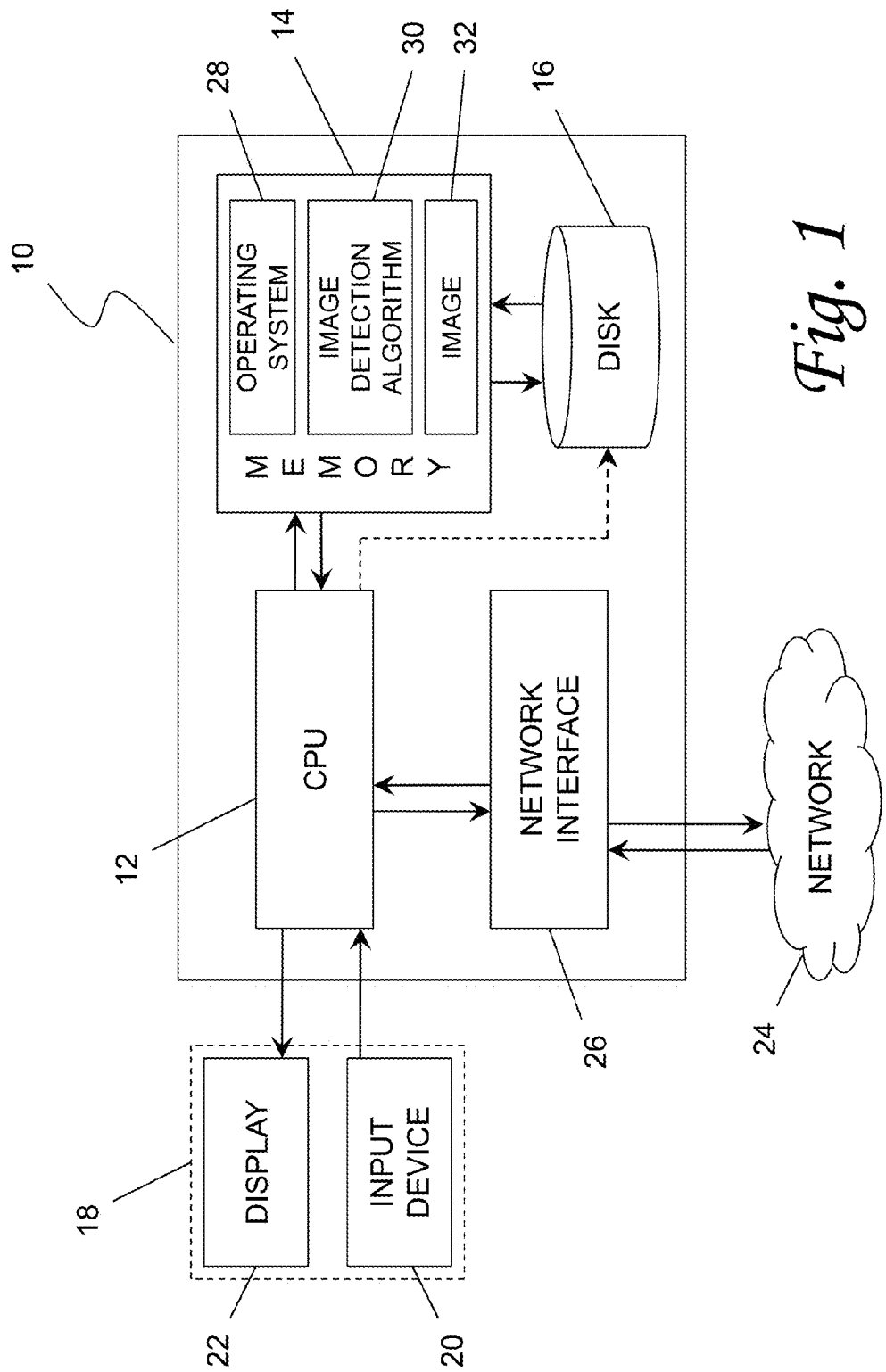
FIG. 1 is a schematic block diagram of an exemplary hardware and software environment for a computer system suitable for implementing an algorithm to detect images consistent with embodiments of the invention.

Turning to the drawings, wherein like numbers denote like parts throughout the several views, FIG. 1 illustrates an exemplary hardware and software environment for an apparatus 10 suitable for implementing an image quality assessment system consistent with embodiments of the invention. For the purposes of the invention, apparatus 10 may represent practically any type of computer, computer system or other programmable electronic device, including a client computer, a server computer, a portable computer, a handheld computer, an embedded controller, etc. Moreover, apparatus 10 may be implemented using one or more networked computers, e.g., in a cluster or other distributed computing system. Apparatus 10 will hereinafter also be referred to as a "computer," although it should be appreciated that the term "apparatus" may also include other suitable programmable electronic devices consistent with embodiments of the invention.

Computer 10 typically includes a central processing unit (CPU) 12 including one or more microprocessors coupled to a memory 14, which may represent the random access memory (RAM) devices comprising the main storage of computer 10, as well as any supplemental levels of memory, e.g., cache memories, non-volatile or backup memories (e.g., programmable or flash memories), read-only memories, etc. In addition, memory 14 may be considered to include memory storage physically located elsewhere in computer 10, e.g., any cache memory in a processor in CPU 12, as well as any storage capacity used as a virtual memory, e.g., as stored on a mass storage device 16 or on another computer coupled to computer 10.

Computer 10 also typically receives a number of inputs and outputs for communicating information externally. For interface with a user or operator, computer 10 typically includes a user interface 18 incorporating one or more user input devices 20 (e.g., a keyboard, a mouse, a trackball, a joystick, a touchpad, and/or a microphone, among others) and a display 22 (e.g., a CRT monitor, an LCD display panel, and/or a speaker, among others). Otherwise, user input may be received via another computer or terminal, e.g., via a client or single-user computer (not shown) coupled to computer 10 over a network 24. This latter implementation may be desirable where computer 10 is implemented as a server or other form of multi-user computer. However, it should be appreciated that computer 10 may also be implemented as a standalone workstation, desktop, laptop, hand-held, or other single-user computer in some embodiments.

For non-volatile storage, computer 10 typically includes one or more mass storage devices 16, e.g., a floppy or other removable disk drive, a hard disk drive, a direct access storage device (DASD), an optical drive (e.g., a CD drive, a DVD drive, etc.), flash memory data storage devices (USB flash drive) and/or a tape drive, among others. Furthermore, computer 10 may also include an interface 26 with one or more networks 24 (e.g., a LAN, a WAN, a wireless network, and/or the Internet, among others) to permit the communication of information with other computers and electronic devices. It should be appreciated that computer 10 typically includes suitable analog and/or digital interfaces (e.g., BUS) between CPU 12 and each of components 14, 16, 18, and 26, as is well known in the art.

Computer 10 operates under the control of an operating system 28, and executes or otherwise relies upon various computer software applications, components, programs, objects, modules, data structures, etc. For example, an image detection algorithm 30 may be resident in memory 14 to analyze image 32 also in memory or alternately resident in mass storage 16. Moreover, various applications, components, programs, objects, modules, etc. may also execute on one or more processors in another computer coupled to computer 10 via the network 24, e.g., in a distributed or client-server computing environment, whereby the processing required to implement the functions of a computer program, such as the image detection algorithm 30, may be allocated to multiple computers over the network 24.

In general, the routines executed to implement the embodiments of the invention, whether implemented as part of an operating system or a specific application, component, program, object, module or sequence of instructions, or even a subset thereof, will be referred to herein as "computer program code," or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable signal bearing media used to actually carry out the distribution. Examples of computer readable media include but are not limited to recordable type media such as volatile and non-volatile memory devices, floppy and other removable disks, hard disk drives, magnetic tape, optical disks (e.g., CD-ROMs, DVDs, etc.), among others.

In addition, various program code described hereinafter may be identified based upon the application within which it is implemented in a specific embodiment of the invention. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the invention is not limited to the specific organization and allocation of program functionality described herein.

Those skilled in the art will recognize that the exemplary environment illustrated in FIG. 1 is not intended to limit the present invention. Indeed, those skilled in the art will recognize that other alternative hardware and/or software environments may be used without departing from the scope of the invention.

Figure 2:
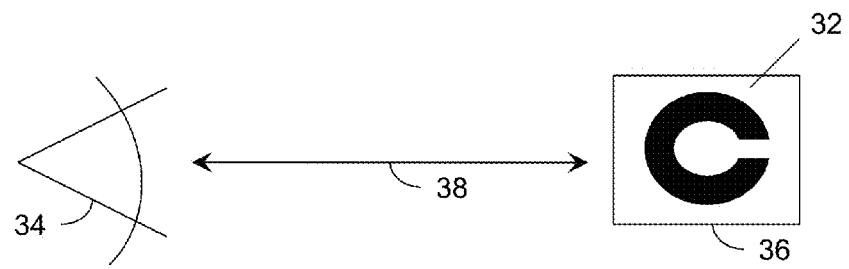
FIG. 2 illustrates a target image to be recognized at a distance from an observer or sensor to be used with the image detection algorithm.

Embodiments of the invention implement an algorithm 30 configured to detect an orientation of a gap in a Landolt C as a resolution target. As illustrated in FIG. 2, a sensor, such as an Infrared (IR), Near Infrared (NIR), or Visual (VIS) sensor, 34 is directed at a target 36. In this illustrated embodiment, images 32 of the target 36 were acquired at multiple distances 38 from the sensor 34 to the target 36 as the method for probing the resolution of the sensor. As discussed above and in alternate embodiments, the size of the Target 36 may also be adjusted, holding the distance 38 constant. Determining the orientation of the gap in the Landolt C is composed of a two step process. First the center of the "C" is determined and then, second, from that center, the orientation of the gap may be determined. In some embodiments, the center of the "C" may be automatically determined using a software algorithm to analyze the image for a fully automatic process. Or, in alternate embodiments, a human observer may indicate the center of the "C" in a semi-automatic process. Regardless of how the center of the "C" is determined, the process to determine the gap orientation is the same. With that in mind, the gap detection algorithm will be discussed first, followed then by a discussion of an algorithm to determine the center of the "C" in the fully automatic process.

Figure 4:
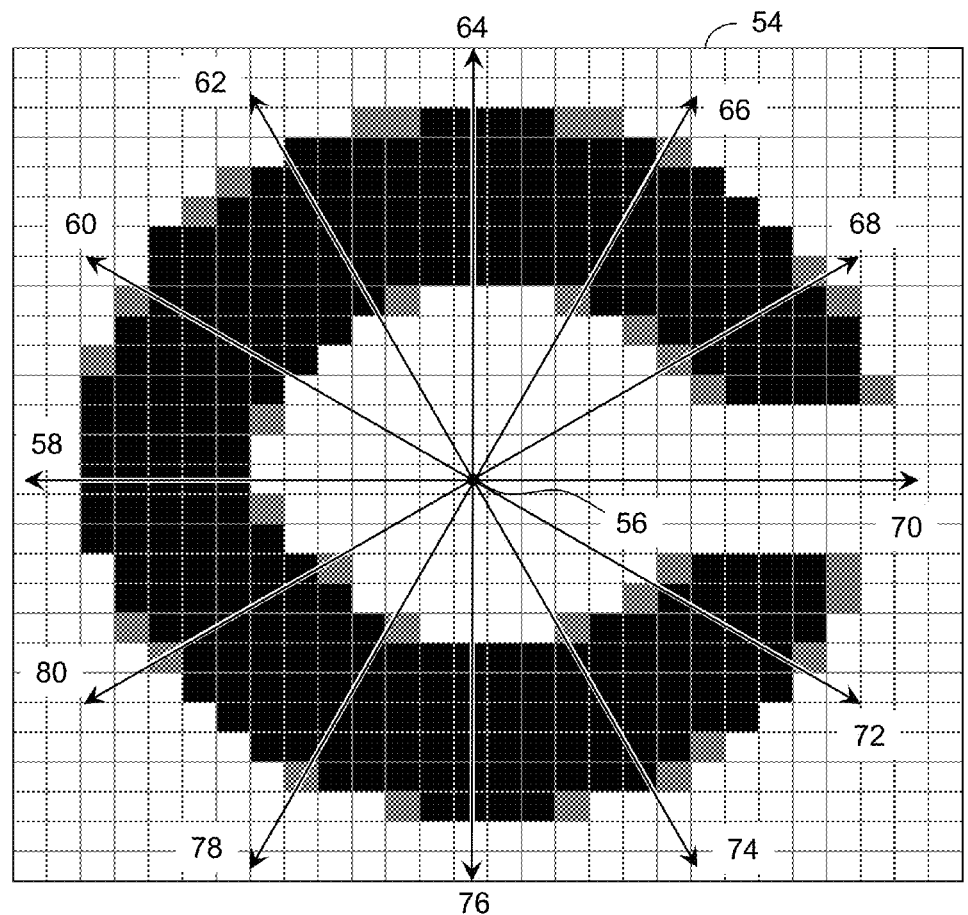
FIG. 4 is a simplified pixelized representation of a Landolt C for use in describing the image detection algorithm.
Figure 3:
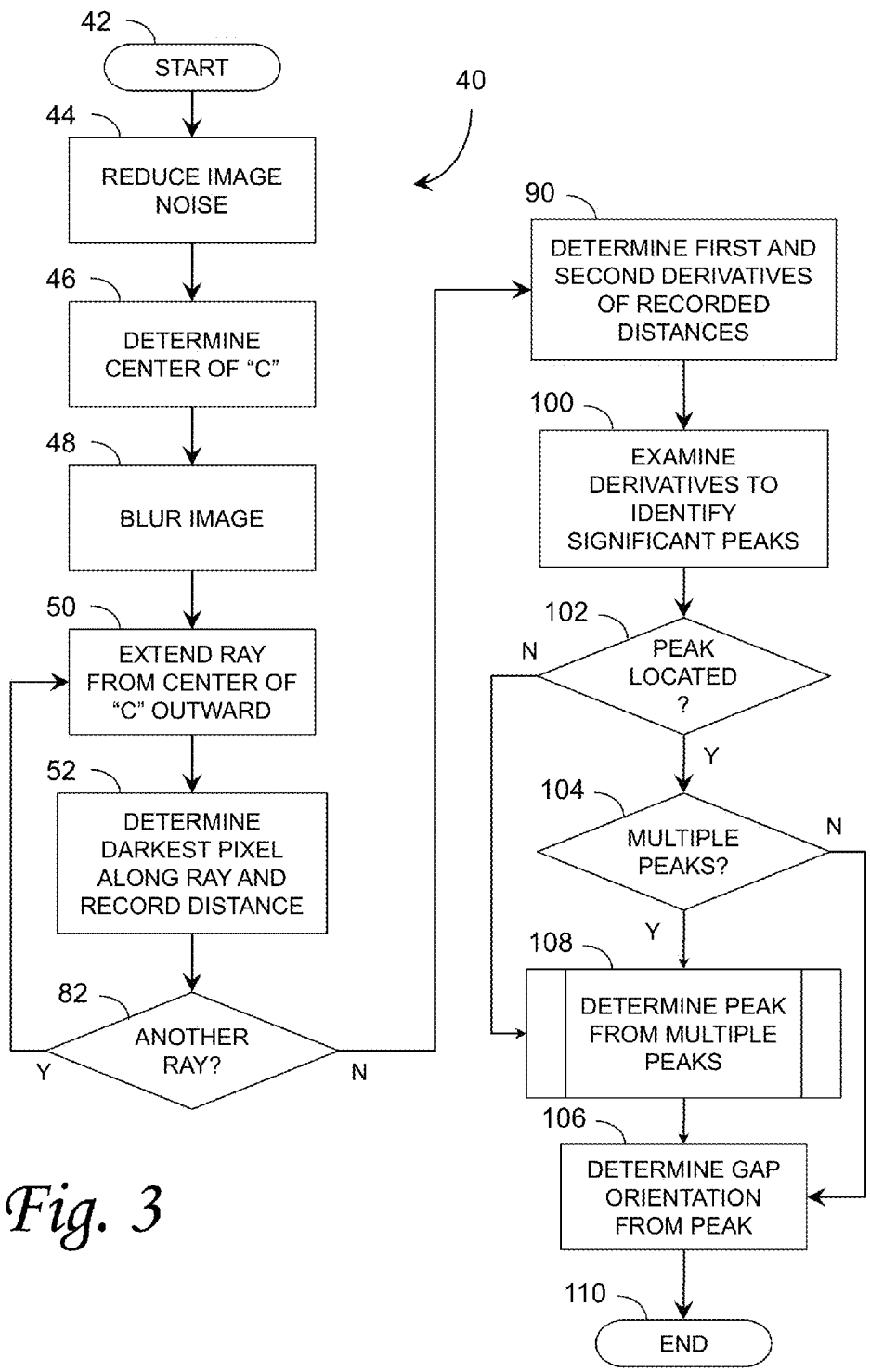
FIG. 3 is a flowchart of a gap detection portion of the image detection algorithm.

Turning to FIG. 3 and flowchart 40, the process begins at block 42. Image noise is reduced at block 44. In some embodiments, the noise may be reduced by averaging multiple frames containing the target image. In other embodiments, other denoising algorithms known to those of ordinary skill in the art may also be used. The center of the "C" in the image is determined at block 46 by either manually by a human observer or automatically as described further below. The image is then blurred at block 48. In some embodiments, the image may be blurred using a Gaussian kernel of size ranging from about 5 to about 15. In a particular embodiment, a Gaussian kernel of size 11 was used. In other embodiments, other blurring algorithms as are known to those of ordinary skill in the art may also be used. A ray is extended from the center of the "C" outward at block 50. A distance from the center to the darkest pixel along the ray is recorded at block 52. To better illustrate this procedure, and referring now to FIG. 4, a simplified and exemplary pixelized version of a Landolt C 54 is presented. The center 56 of the "C" is also shown for illustration purposes. A first ray 58 is drawn from the center 56 of the "C" outward. The dark pixel is the seventh pixel from the center and a distance of 7 is recorded, representing the length from the center. In this simplified version containing only three colors, black, dark gray, and white, it is easy to determine the distances. In practice, however, the image may contain pixels ranging through many shades of gray based on the image quality and the distance 38 to the target 36 on the image 32. Other factors related to image manipulation may also introduce additional shades of gray which may be encountered while traversing the ray. Moreover, while this example shows only three colors, black, dark gray, and white, and the description above refers to grayscale images, color images may also be analyzed in some embodiments.

Figures 5, 6:
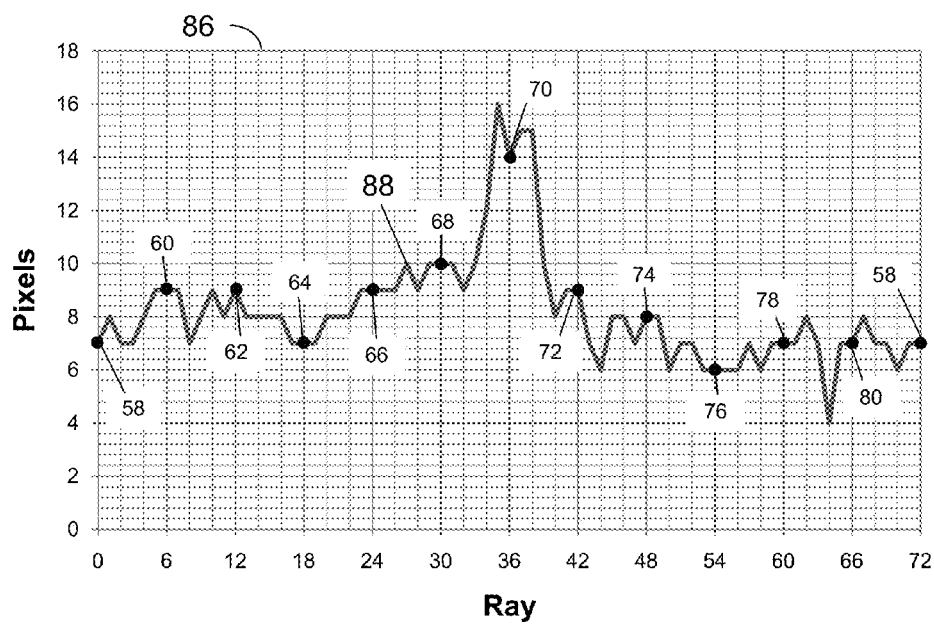
FIG. 5 is a table of pixel values gathered as part of the image detection algorithm.
FIG. 6 is a graph including the pixel values from the table in FIG. 5.

This process is then repeated with additional rays 60-80 around the "C", each defining and recording a distance from the center to a dark pixel. For example, in FIG. 4, the distance from the center to a dark pixel along ray 64 is seven pixels (ray crosses through 7 pixels to get from center to dark pixel), while the distance along ray 68 is ten pixels. Returning to FIG. 3, if there are additional rays ("YES" branch of decision block 82), then a distance is determined for those rays until all of the rays have been processed (blocks 50, 52). In the example in FIG. 4, twelve rays were illustrated, however, data was collected using 72 rays. In a particular embodiment, the algorithm may use 100 rays in order to attempt to capture the detail of the "C" and more particularly the gap orientation. In other embodiments, more or fewer rays may be used depending on the level of detail required during analysis and the amount of compute power available to process the rays. Table 84 in FIG. 5 shows the data from the twelve rays 58-80 used in FIG. 4. A similar table or array of values may be created for the embodiments employing more rays. For example, the array for the embodiment with 100 rays will contain 100 distance values.

Figure 7:
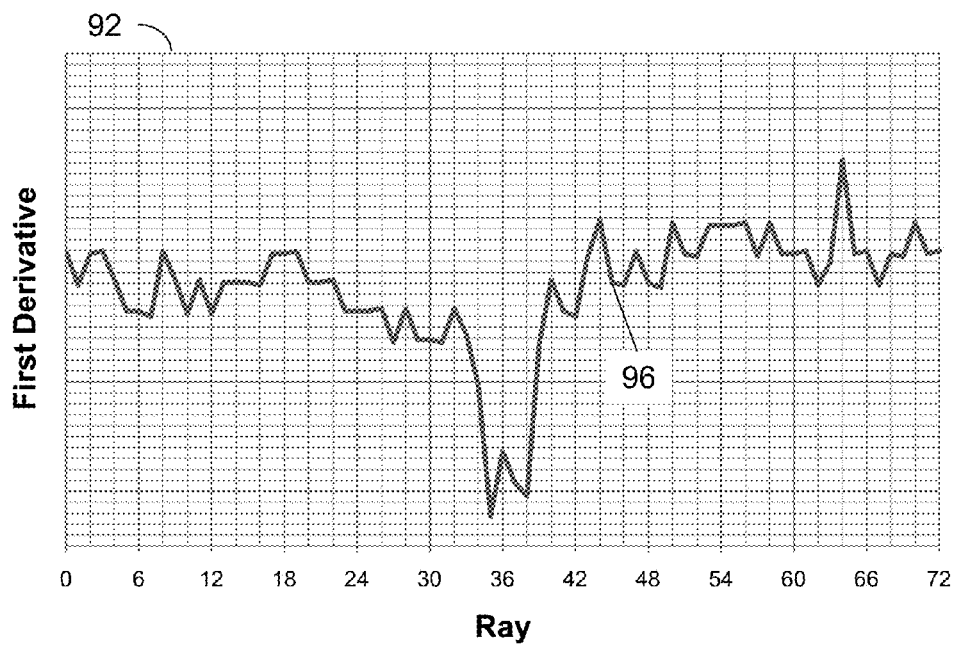
FIG. 7 is a graph of the first derivative of the graph in FIG. 6.
Figure 8:
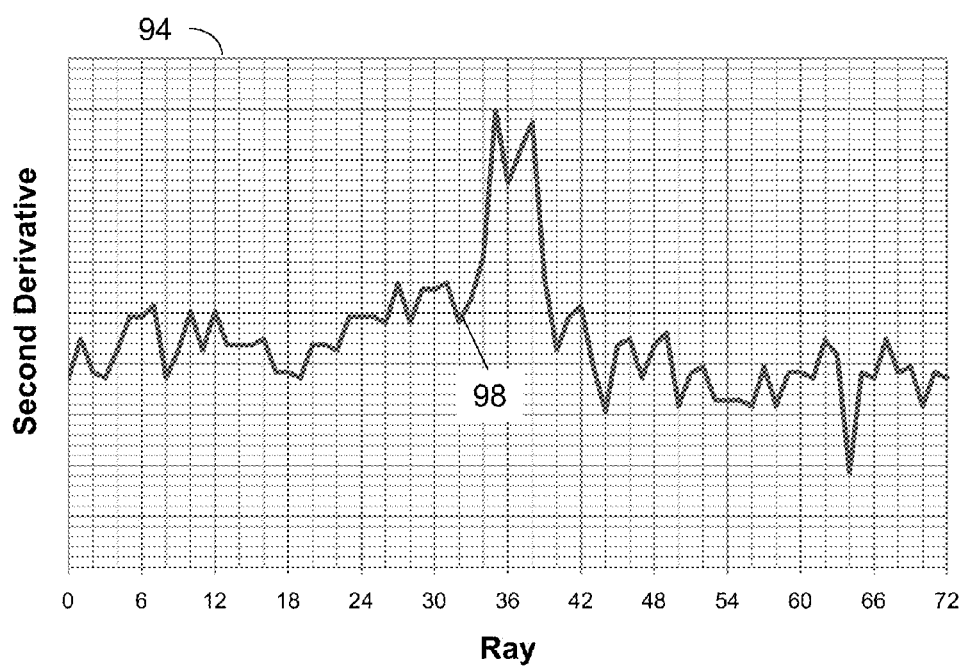
FIG. 8 is a graph of the second derivative of the graph in FIG. 6.

This array exhibits signal like characteristics as can be seen when plotted in graph 86 in FIG. 6. Curve 88 representing the data points exhibits a series of peaks and valleys. Due primarily to the simplistic nature of the example, a large peak exists near the ray 70 and thus would likely indicate the orientation of the gap from the "C" to be in the direction of that ray. However in practice, such a dominant peak may not be so readily recognizable or there may be multiple peaks and valleys in the data, any of which may be candidates for determining the orientation of the gap. To assist with the analysis and returning to FIG. 3, first and second derivatives of the "signal" type data compiled from the rays are calculated in block 90. Examples of the first and second derivatives can be seen in the graphs 92 and 94 in FIGS. 7 and 8. Curve 96 in graph 92 represents the first derivative of the data and curve 98 in graph 94 represents the second derivative of the data. As can be seen in the graphs 92, 94 of the derivatives the curves contain peaks and valleys (maxima and minima). Of these, the peaks are generally the most interesting as they represent orientations where the ray could pass from the center to completely outside the C without hitting a black (or dark) pixel.

Returning again to FIG. 3, the derivatives are examined in block 100 to assist in identifying significant peaks. If a peak is located ("YES" branch of decision block 102), and if there is only one sharp peak in the signal ("NO" branch of decision block 104), then an assumption is made that this single sharp peak represents the gap in the C and the gap orientation is determined from the ray corresponding to the sharp peak in block 106. In the exemplary embodiment with 72 data points or samples, each direction covers about 18 samples. In the embodiment with 100 samples, each direction covers about 25 samples. In the exemplary embodiment, the zero degree position was associated with a leftward directed gap, with 90° corresponding to an upward directed gap, 180° corresponding to a rightward directed gap, and 270° associated with a downward directed gap. The direction and starting point are arbitrary, and therefore, other starting locations and/or a counter-clockwise rotation may also be used in other embodiments. For example, the 100 sample embodiment may associate the zero degree position (sample data points zero to 24) with a rightward directed gap, with 90° (sample data points 75 to 99) corresponding to an upward directed gap, 180° (sample data points 50 to 74) corresponding to a leftward directed gap, and 270° (sample data points 25 to 49) associated with a downward directed gap. In the simplistic example in FIG. 4, ray 70 is in the center of the 72 rays and corresponds to about 180°. Therefore, the orientation of the gap detected by the algorithm for this example is located to the right of the "C".

Otherwise, if there are multiple peaks ("YES" branch of decision block 104) or if a dominant peak is not located ("NO" branch of decision block 100), then all of the peaks are analyzed in block 108 as set out in more detail below. After determining a peak or other indicator corresponding to at least one ray, the orientation of the gap is detected at block 106. The process ends at block 110.

Figure 9A:
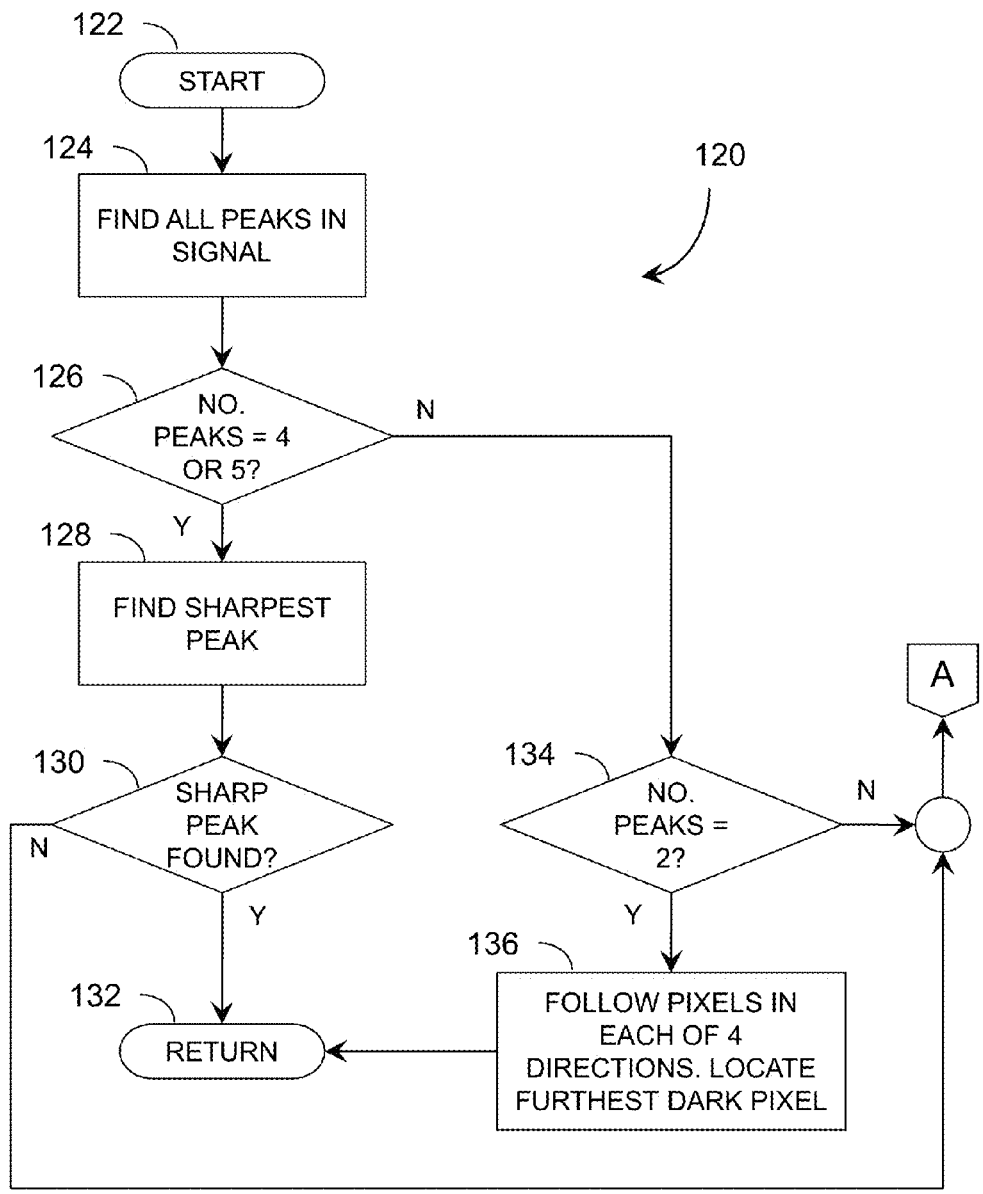
FIGS. 9A and 9B are a flow chart illustrating the peak detection portion of the image detection algorithm of FIG. 3.
Figure 9B:
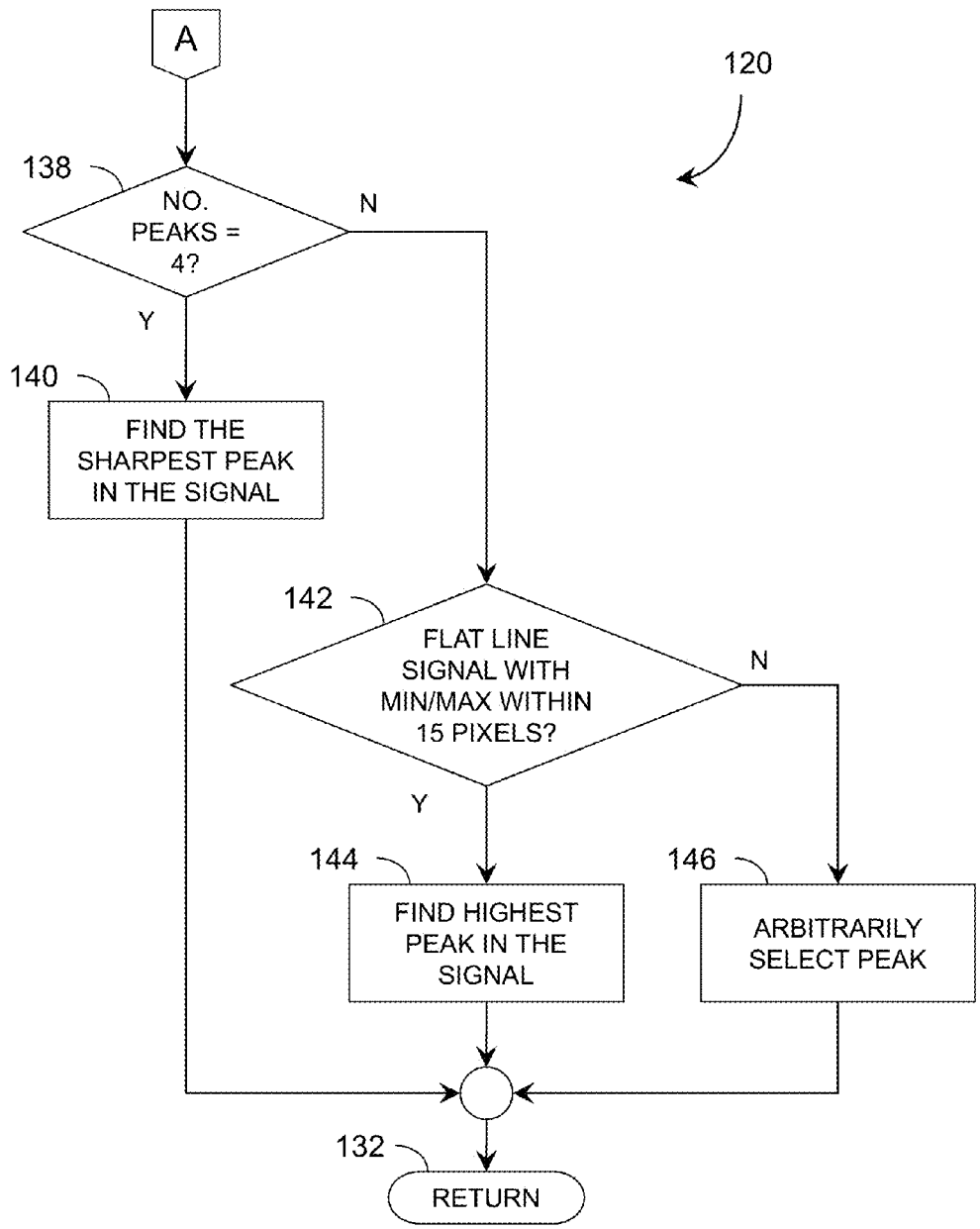

Multiple peaks may be analyzed (process block 108 in flowchart 40) using a method depicted by flowchart 120 in FIGS. 9A-9B in some embodiments. Peak detection starts at block 122. All of the peaks of the signal are found based on size, location, and category in block 124. If the number of peaks found equals four or five ("YES" branch of decision block 126), the sharpest peak of the peaks is found in block 128. In some embodiments, the sharpest peak may be defined as the peak with largest height to width ratio, though other definitions for a sharp peak may also be used. If a sharp peak is found ("YES" branch of decision block 130), then that sharp peak is used to determine the orientation for the gap in the Landolt C as set out above. The method returns to block 106 of flowchart 40 at block 132. Otherwise, if the number of peaks is not four or five ("NO" branch of decision block 126), then a check is made to determine if the number of peaks is equal to two.

If the number of peaks is two ("YES" branch of decision block 134), then pixels are followed in each of the four directions to locate the darkest pixel in block 136.

The direction is selected where the darkest pixel is furthest away and used to determine the orientation for the gap in the Landolt C as set out above. The method then returns to block 106 of flowchart 40 at block 132. Alternatively, and in some embodiments, the direction may be determined by, from the center, finding the brightest pixel in each of the four orientations (up, down, left, right) while also considering contributions from the diagonal pixels (upper right, upper left, lower right, lower left). The brightest pixel may be used to define the direction which is then used to determine the orientation for the gap in the Landolt C as set out above.

If the number of peaks is not two ("NO" branch of decision block 134) or a sharp peak was not found ("NO" branch of decision block 130), then a check is made to determine if the number of peaks equal four. If the number of peaks is four ("YES" branch of decision block 138), then the sharpest peak is located in the signal at block 140 and the method returns to block 106 of flowchart 40 at block 132. Otherwise, if the number of peaks is not four ("NO" branch of decision block 138), then a check is made to determine if the signal is a flat line type signal where the minimum and maximums of the signal are within about 15 pixels. If the signal is a flat line type signal ("YES" branch of decision block 142), then the highest peak in the signal is located at block 144 and the method returns to block 106 of flowchart 40 at block 132. Otherwise, if the signal is not a flat line type signal ("NO" branch of decision block 142), the peak/direction is arbitrarily selected at block 146. In some embodiments, the arbitrary selection may be a default to a particular orientation, while in other embodiments; the arbitrary selection may be a random selection of one of the four orientations. After the arbitrary selection, the method returns to block 106 of flowchart 40 at block 132.

Other embodiments may employ other methods for determining the highest peak. For example, in an alternate embodiment, the peak may be determined by first locating the white center (or nearly white center) of the "C". A peak limit may be set, such as to about seven, though other values may be used in other embodiments. The signal may then be searched for the highest peak and lowest valley that are separated by "peak limit" pixels. If the highest peak is found, then that peak may be used to determine the orientation of the "C". Otherwise, the peak limit may be decremented and the process repeated. When the peak limit reaches zero, then an arbitrary selection or other method may be invoked.

Figures 10, 12:
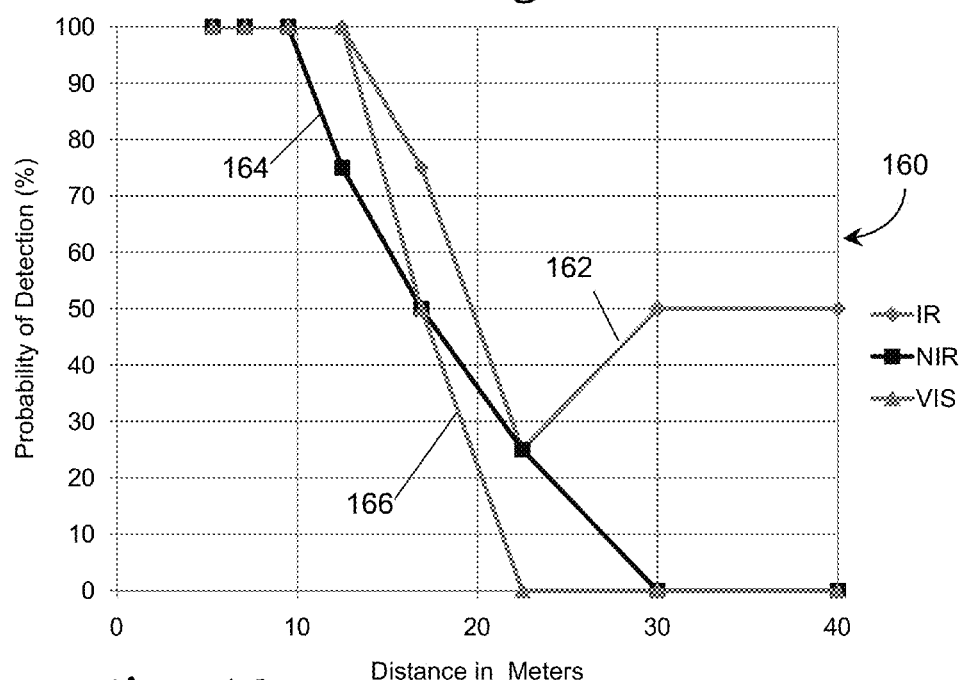
FIG. 10 is a table representing results from images acquired from various sensors at various distances.
FIG. 12 is a graph of the data in the table in FIG. 10.
Figure 11:
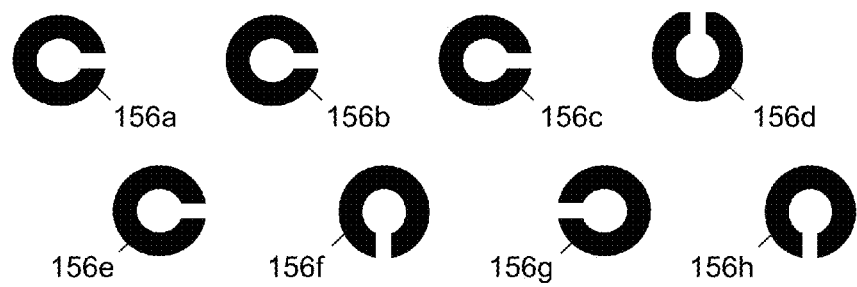
FIG. 11 is a graphical representation of exemplary orientation results of the Landolt C for a particular sensor.

The table in FIG. 10 illustrates table 150 containing exemplary data 154, 156, 158 for images generated respectively by an IR, NIR, and VIS sensor at several distances 152. A series of images from each of these sensors may be generated at each of the distances 152 and evaluated with the image detection algorithm set out above. Results from the algorithm for one such series for an NIR sensor may be similar to the exemplary orientations of the Landolt Cs 156a-156h illustrated in FIG. 11. The combined results (in percentage correct) 154-158 may then be determined based on the output of the algorithm and the actual orientation of the Landolt C on target 36. This data can then be plotted on graph 160 as illustrated in FIG. 12 showing "frequency of seeing" curves 162, 164, and 166 for each of the respective IR, NIR, and VIS sensors.

This data may now be used as an initial screening of sensors in order to reduce the number sensors to a select few that may then be subjected to testing by multiple human observers. Alternately, the data may then be used as a "quick and dirty" evaluation of a number of sensors to assist in selecting a sensor when the funding or time does not permit an exhaustive test by human observers. Even in the semi-automatic mode, the algorithm removes the need to conduct exhaustive testing by human observers for a first pass or "quick and dirty" analysis. Furthermore, the data can be used to evaluate digital images combined, overlaid, or otherwise enhanced to again limit the combinations before presenting these enhanced images to actual human observers. Additionally, the Landolt C gap detection algorithm may also be used in conjunction with other image detection algorithms, such as a Triangle Orientation Detection algorithm as discussed in co-pending U.S. application Ser. No. 13/025,570. The use of multiple detection algorithms may present a better evaluation of a sensor or image resolution or quality.

Figure 13A:
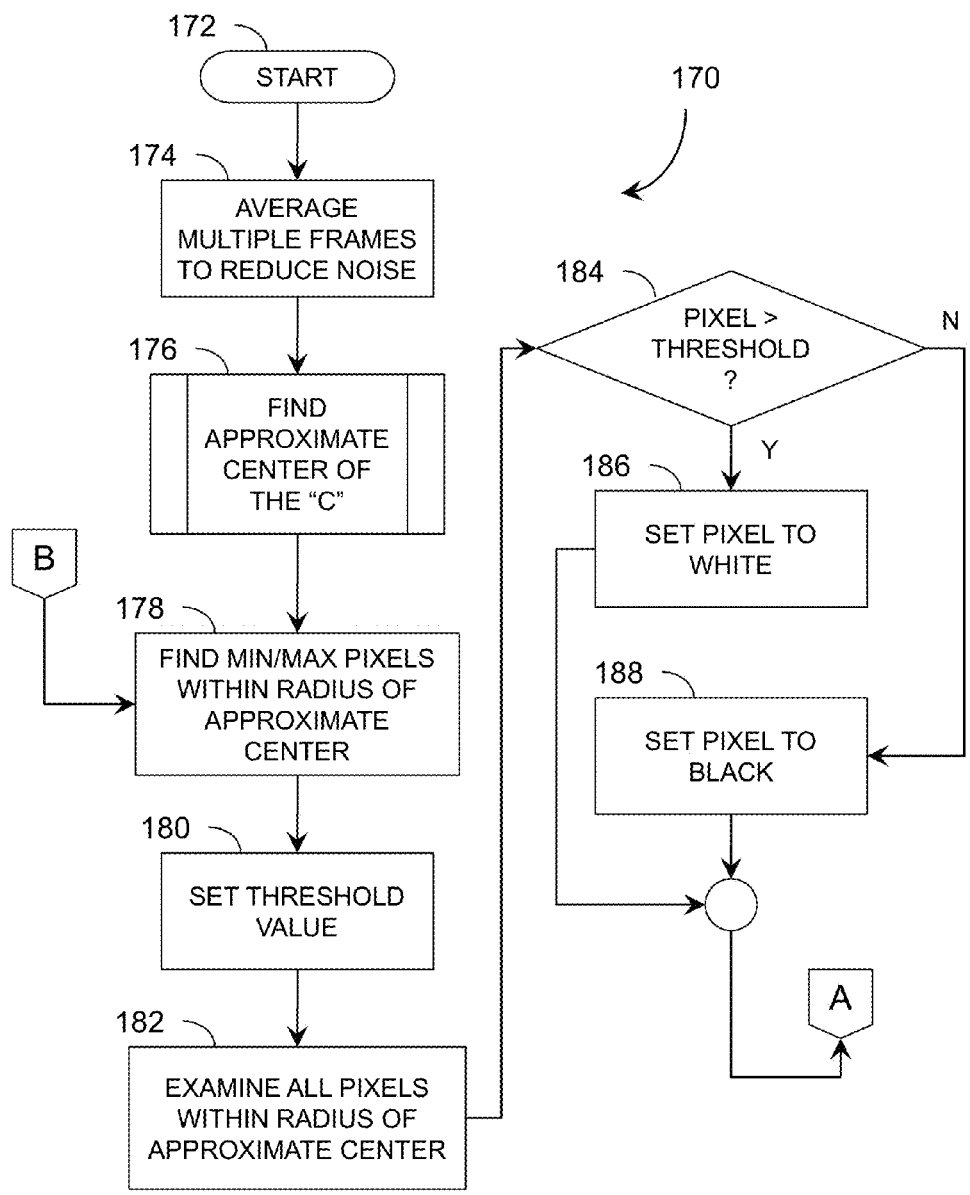
FIGS. 13A and 13B are a flowchart illustrating a center detection portion of the image detection algorithm.
Figure 13B:
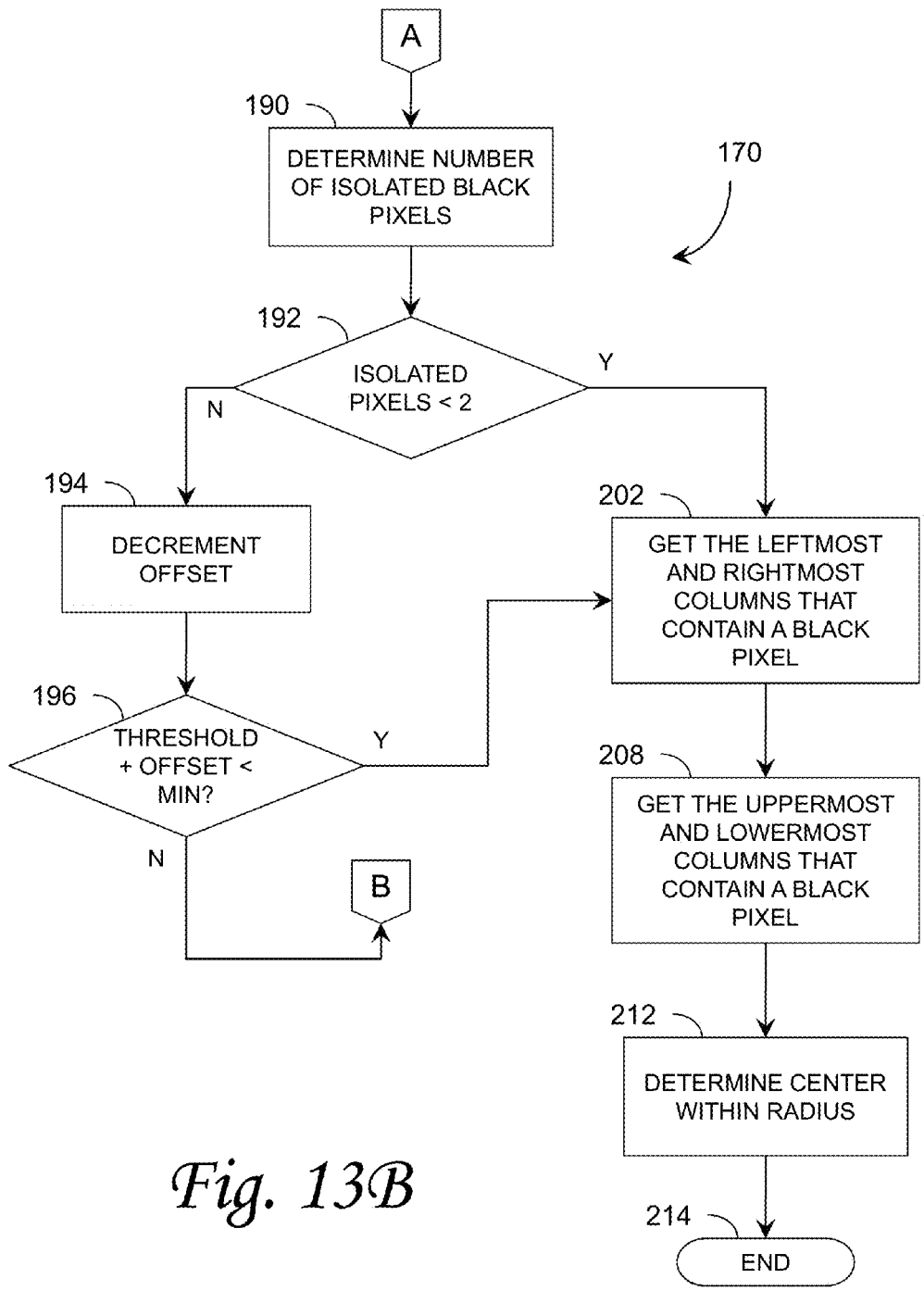

As discussed above, the orientation detection algorithm 30 may be a semi-automatic method, where a human observer indicates the center of the Landolt C on each of the images. The orientation detection algorithm 30 may also be implemented, in some embodiments, as a fully automated detection algorithm, where the algorithm determines the location of the center of the "C" prior to determining the orientation. In some of these embodiments, this may be accomplished as illustrated in flowchart 170 in FIGS. 13A and 13B. The process begins at block 172. To assist in reducing the noise in the image, multiple frames of the same image are averaged at block 174, though other noise reduction algorithms that are known in the art may also be used to reduce the noise in the image. The approximate center of the "C" is found at block 176. This approximate center may now be used for further determination of the actual center of the "C". All of the pixels are examined within a radius of the approximate center of the "C" to determine the minimum and maximum pixels in block 178. In some embodiments, the radius chosen may be large enough to encompass the "C", thus trimming any other pixels that may be noise outside of the "C" and reducing the amount of computation.

A threshold may then be calculated based on the minimum and maximum pixel values in block 180. In some embodiments, this threshold value may be the minimum pixel value plus one quarter of the difference between the maximum and minimum pixel values plus an additional offset which may be related to image size or other image properties. Other embodiments may determine the threshold value differently. Each of the pixels within the radius of the approximate center is examined in block 182 in order it binarize the pixels. If the pixel is greater than the threshold ("YES" branch of decision block 184), then the pixel is set to white in block 186. Otherwise ("NO" branch of decision block 184), the pixel is set to black in block 188. The number of black pixels that do not touch any other black pixel are counted in block 190. These isolated pixels represent noise generated by the binarization process above. If there is more than one isolated pixel ("NO" branch of decision block 192), then the offset is decremented in block 194. If the threshold plus the offset is not less than the minimum pixel ("NO" branch of decision block 196), then the process is repeated with the new threshold value at block 178.

Figure 14:
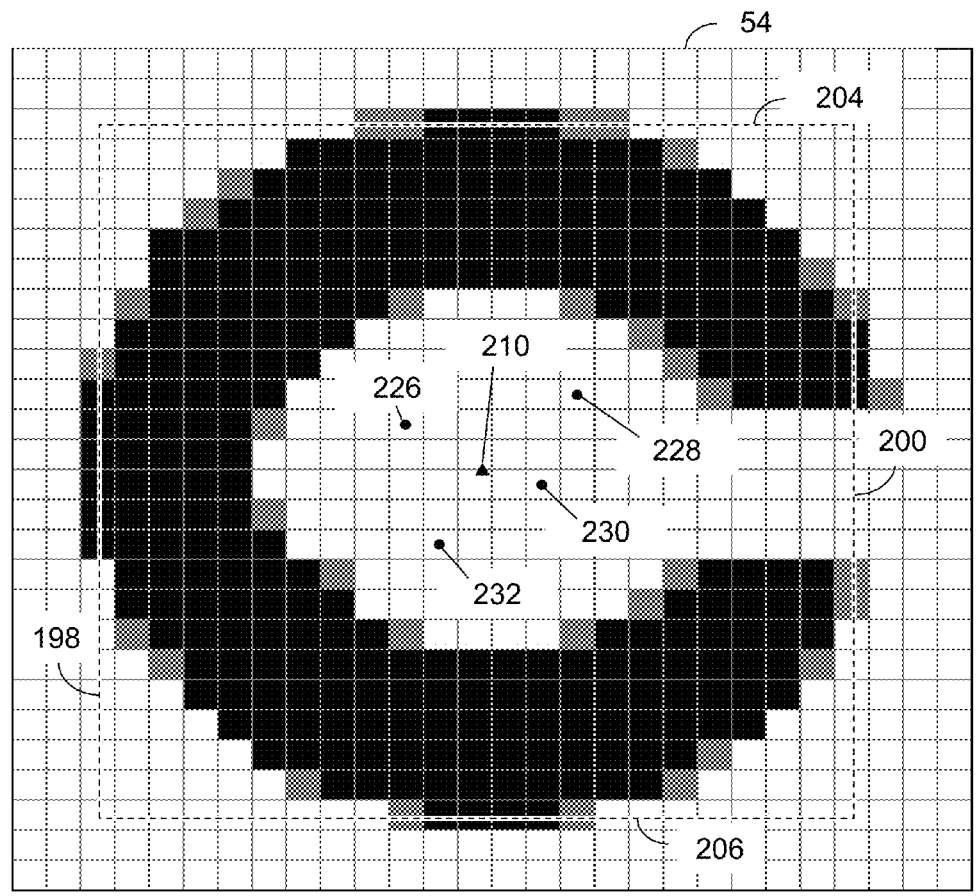
FIG. 14 is a simplified pixelized representation of a Landolt C for use in describing the center detection portion of the image detection algorithm.

Otherwise, if the threshold plus the offset is less than the minimum pixel ("YES" branch of decision block 196) or if there are less than two isolated pixels ("YES" branch of decision block 192), then from the approximate center, the leftmost and rightmost columns (198 and 200 respectively in FIG. 14) of the image 54 that contain a black pixel are retrieved in block 202. Similarly, the uppermost and lowermost columns (204 and 206 respectively in FIG. 14) of the image 54 that contain a black pixel are retrieved in block 208. From these columns, forming a rectangle, the center of the "C" (210 in FIG. 14) may be located at block 212. The process ends at block 214. At this point, the center of the "C" is now known and the orientation of the "C" may now be determined using the process set out in the embodiments above.

The above embodiment for determining the center of the "C" finds an approximate center of the "C" at block 176 of flowchart 170. In some embodiments, the approximate center may be found as set out in flowchart 220 in FIG. 15. The process begins at block 222. A list of possible centers is generated at block 224, such as centers 226, 228, 230, and 232 illustrated in FIG. 14. A center of mass is calculated for all of the possible centers and any of the possible centers in the list that are outliers based on the calculated center of mass are removed from the list at block 234. A moving average for the image category is calculated at block 236. The moving average, in some embodiments, may be the list of centers determined from previous images. These centers may be dependent on the image category, such as images created by IR, NIR, VIS, etc. sensor since each of these image capturing type devices may not be directly inline with the target image 36, but rather at some small angle off of the center. These known positions of the sensors allow for adjustments to the moving average. In embodiments with a single sensor in a direct line with the target image 36, it may not be necessary to track the image category.

Centers from the list of possible centers that are too far from the moving average are removed at block 238 and an updated list of the remaining possible centers is generated at block 240. If there are suitable centers remaining after removing those that are too far from the moving average ("NO" branch of decision block 242), a new center of mass is calculated from the remaining centers and any of the possible centers remaining in the list that are outliers based on the calculated new center of mass are removed from the list at block 244. Otherwise, if there are no suitable centers remaining ("YES" branch of decision block 242), then the center from the moving average is used at block 246.

Figure 16:
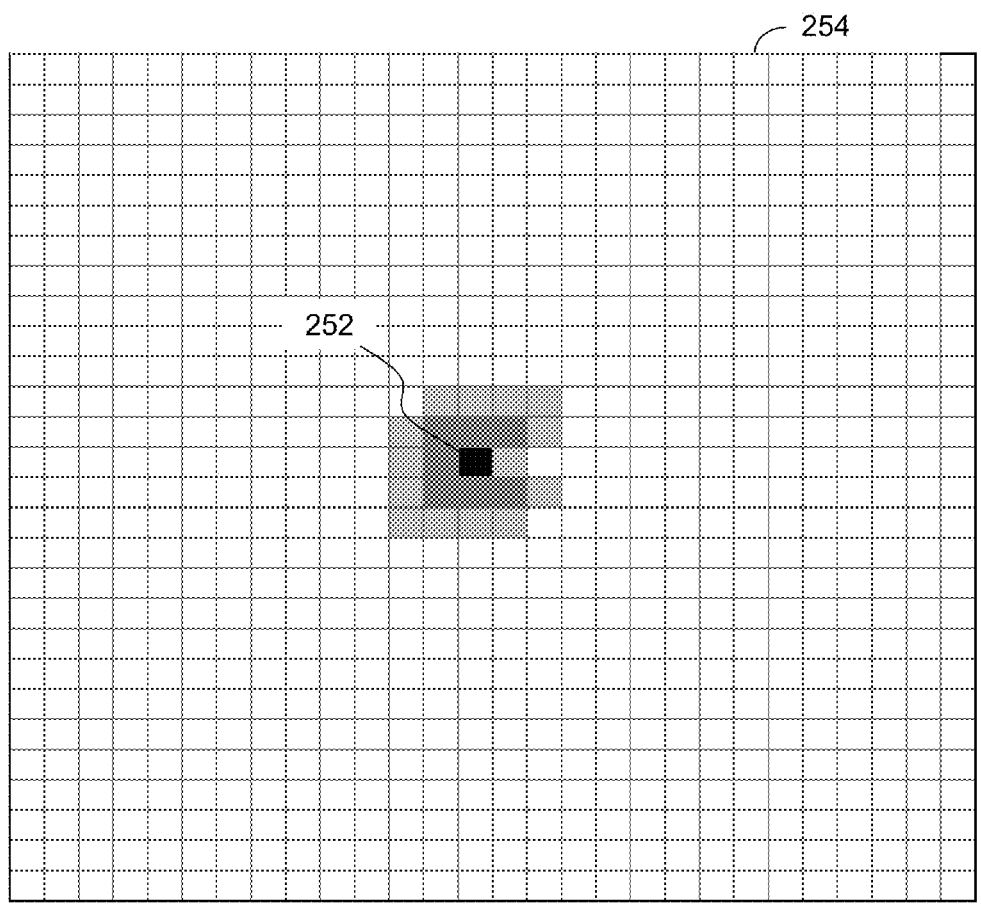
FIG. 16 is a simplified pixelized representation of a Landolt C for use in describing the center detection portion of the image detection algorithm.

The possible centers are then ranked at block 248 from most likely to least likely possibilities. The information gathered during the generation of the list of centers is used to calculate the rank for each point in the list. If no suitable centers are available, e.g., for images where the "C" is located at one of the further distances, then the darkest, closes pixel is found that lies close to a possible center point at block 250, such as pixel 252 in the exemplary "C" in image 254 in FIG. 16. This is a pixel 252 that has the highest confidence of being the center of the "C". The process returns with the identified approximate center to block 176 of flowchart 170 in FIG. 13A at block 256.

Figure 17A:
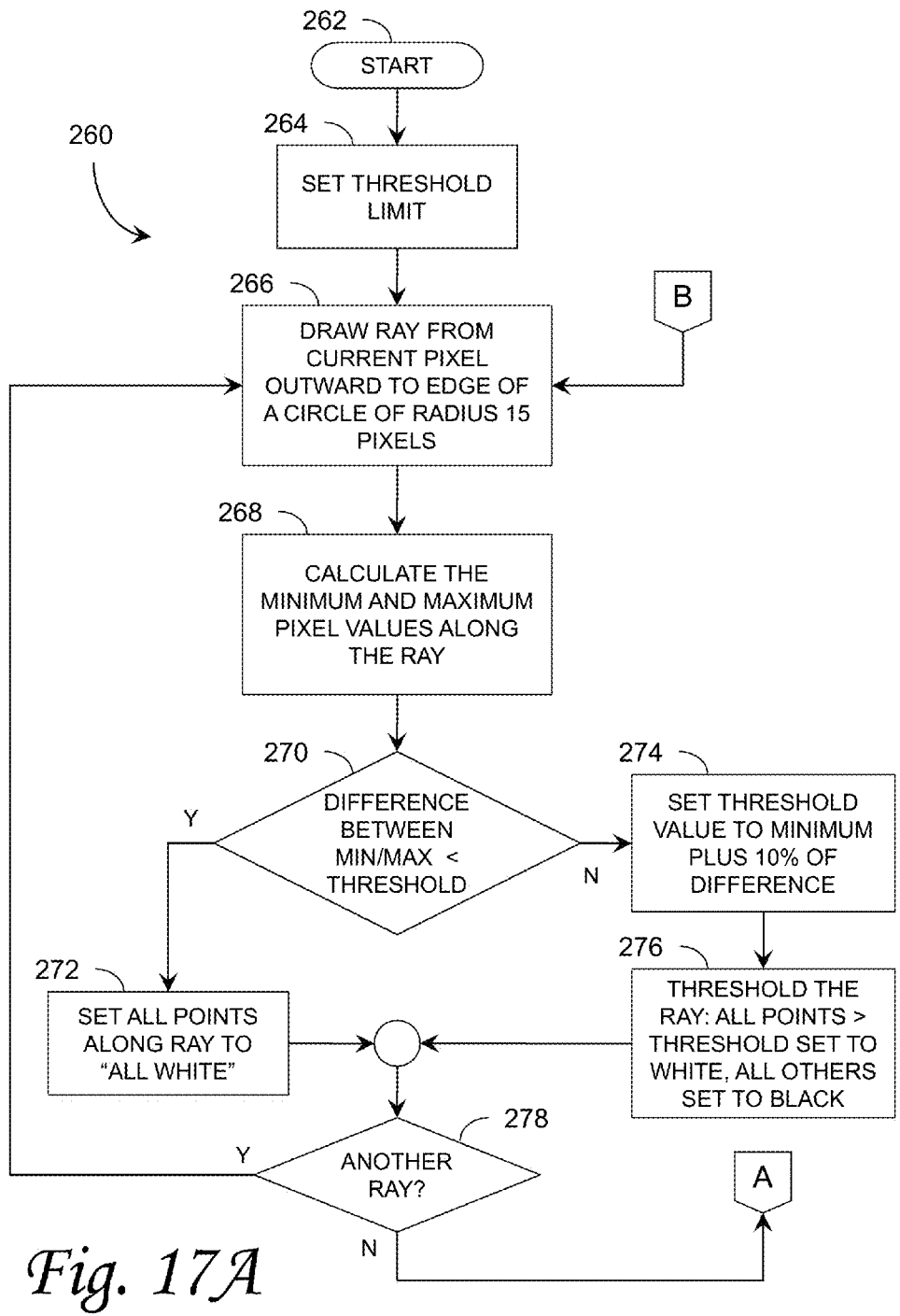
FIGS. 17A-17C are a flowchart illustrating a portion of the center detection portion of the image detection algorithm.
Figure 17B:
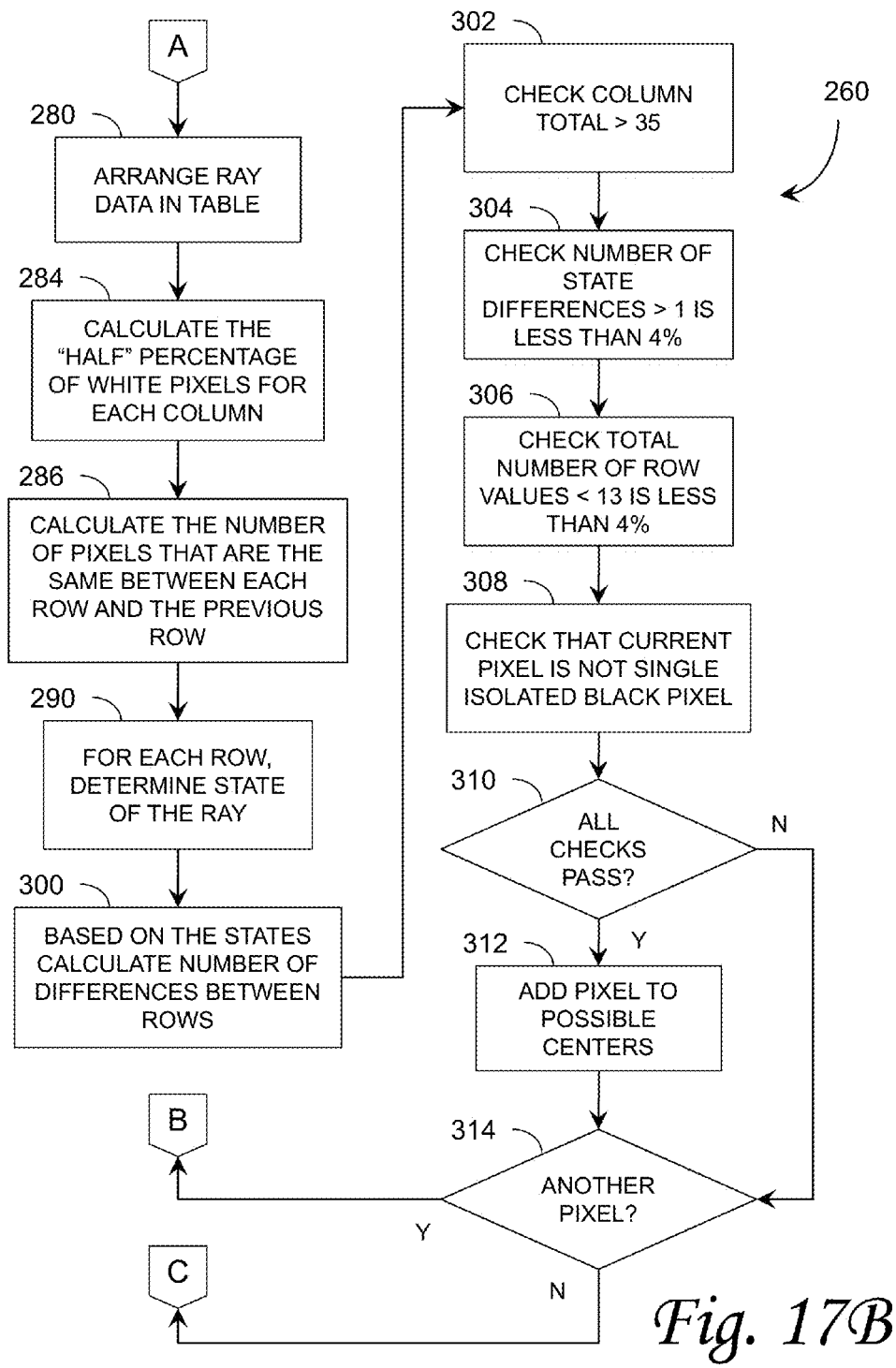
Figure 17C:
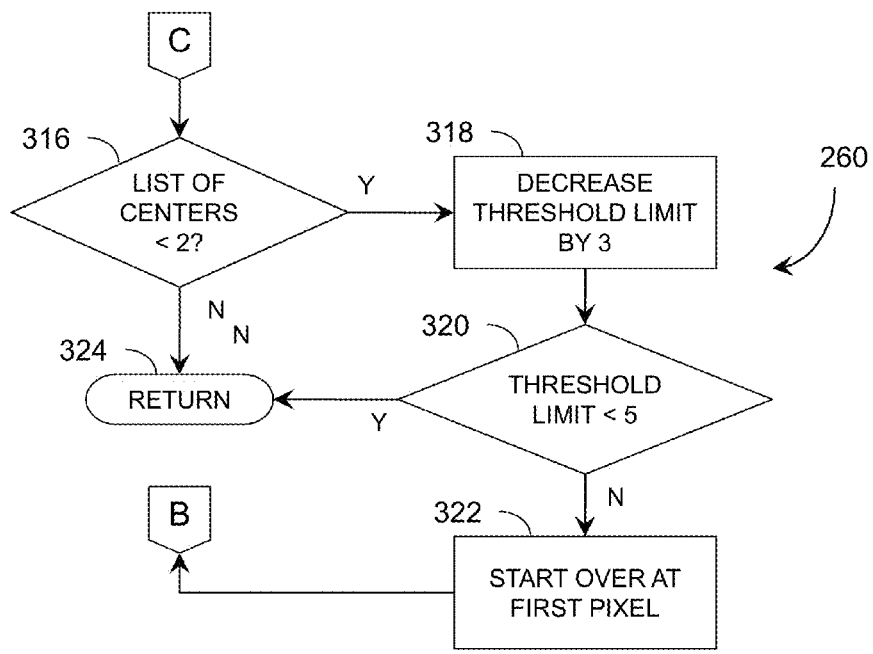

The above embodiment for determining the approximate center of the "C" generates a list of possible centers of the "C" at block 224 of flowchart 220. In some embodiments, the list of possible centers may be found as set out in flowchart 260 in FIGS. 17A-17C. The process begins at block 262. A threshold limit is set at block 264. In some embodiments, this threshold may be set to a value of 39 initially, though other values for other embodiments may also be used. The threshold limit represents the allowable minimal difference between a minimum and maximum pixel along a ray. For each pixel in the image, pixels surrounding the current pixel may be binarized radially in a series of angular steps, though in other embodiments, other binarization methods may be used. In a particular embodiment, about 200 angular steps may be used, but more or fewer steps may also be sufficient. At each of these steps, a ray is drawn radially from the current pixel to the edge of a circle surrounding the pixel at block 266. The radius of this circle can vary and may dependent on the resolution of the image being processed. In a particular embodiment, the radius for the circle is about 15 pixels.

The difference between the minimum and maximum pixel along the ray is calculated at block 268. If the difference between the minimum and maximum pixel is less than the threshold limit ("YES" branch of decision block 270), then all of the points along the ray are set to white at block 272. The points may be located at equally spaced intervals along the ray. If a point does not fall exactly on a pixel (as most will not) a linear interpolation between the four closest pixels may be performed to determine a "virtual" pixel value to be used for that point. In other embodiments, other interpolation methods may be employed, or some embodiments may not interpolate but rather use the closest actual pixel value. If the difference between the minimum and maximum are greater than the threshold limit ("NO" branch of decision block 270), then a separate threshold may be defined and set to the minimum pixel plus ten percent of the difference between the minimum and maximum pixels at block 274. All points along the ray are compared to the new threshold and those that are greater than the threshold are set to white while the remaining points are set to black at block 276. If there is another ray ("YES" branch of decision block 278), then the process repeats for the new ray at block 266.

Figure 18:
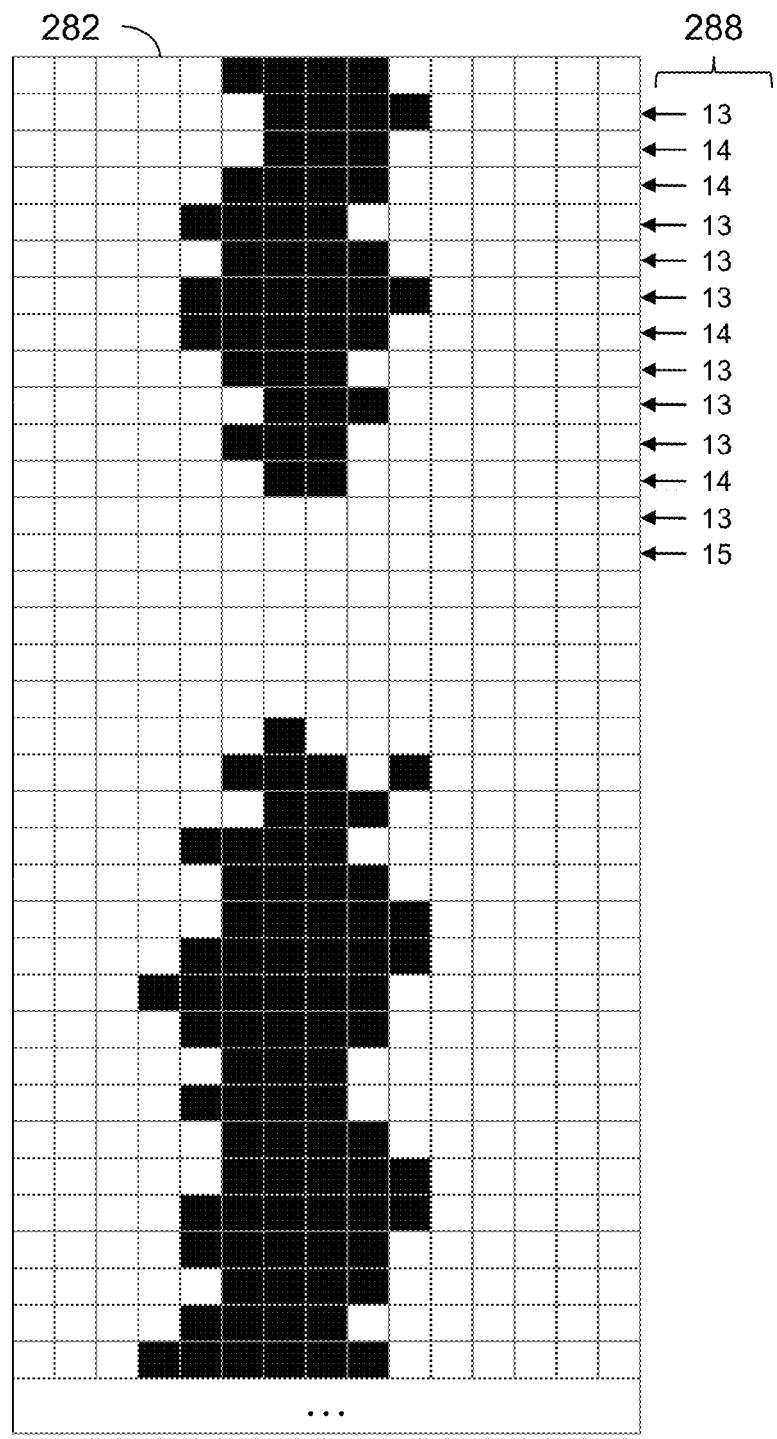
FIG. 18 is an exemplary graphical representation of a table of binarized values from the center detection portion of the image detection algorithm.

If there are no more rays to be processed ("NO" branch of decision block 278), the data from the rays for the pixel is arranged in a table at block 280. This data table contains columns matching the number of points along the ray, about 15 in this particular embodiment, and rows matching the number of rays used to binarize around the pixel, about 200 in this embodiment. In other embodiments, the rows and columns may also be reversed. Table 282 in FIG. 18 is a graphical illustration of such a table with each row representing a ray. For each of the columns in the table, a "half" percentage is calculated at block 284. In order to calculate the half percentage, the percentage of the number of pixels that are white in the column is calculated and then that percentage is divided by two. In this particular embodiment with 15 columns, there will be 15 half percentages calculated. While a half percentage is used in this embodiment for a measure on each of the columns in the table, other embodiment may employ other methods to evaluate the contents of the columns. For example the full percentage may be used or the percentage of black pixels, rather than white, may be used in other embodiments.

Figure 19:
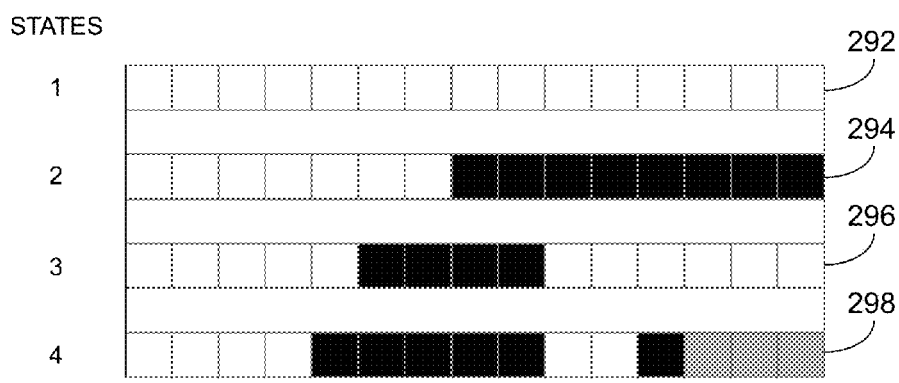
FIG. 19 is a table illustrating different states of data in the binarized table of FIG. 18.

For each row, a number of pixels that have not changed from the previous row is determined in block 286. An example of exemplary row results 288 can be seen next to their respective rows using exemplary table 282 in FIG. 18. Additionally a state for each row is determined at block 290. FIG. 19 illustrates the four different states that may be assigned to a row. The first state 292 is an all white row. The second state 294 is a row that starts out white and changes to black. The third state 296 is a row that starts out white, changes to black, and then back to white again. And the fourth state 298 is a row that starts out white, changes to black and contains noise. Using the states, a starting position of the black stripe is recorded along with the length of the black stripe and whether there is any noise for each of the rows. From this information, the number of differences between each row and the previous row is calculated in block 300. In some embodiments, a difference in starting position counts as one; a difference in length counts as another one; noise also counts as one. Therefore there can be as few as zero or as many as three differences between rows. The number of differences is recorded for each of the rows. One of ordinary skill in the art will recognize that other states (more or fewer) and other difference measures may also be used to characterize each of the rows.

After the calculations have been performed on the data in the table 282, a check is made for each of the column half percent totals to make sure they are greater than 35 in block 302. Using the number of state differences numbers from above, the number of rows is counted where the row has a number greater than one. A check is made to determine if this count is less than four percent of all of the rows in block 304. Using the row totals 288, the number of rows that have a total less than 13 (signifying that more than 2 pixels have changed from the previous row) are counted. A check is made to determine if this count is less than four percent of all of the rows at block 306. And finally, a check is made after thresholding radially, that the current pixel is not a single isolated black pixel in block 308. If all of the above checks pass ("YES" branch of decision block 310), then the pixel is added to the list of possible centers at block 312. While all of the checks performed for this illustrated embodiment are used to determine a possible center, other embodiments may utilize only a subset of the checks or different checks on the data in the table 282 to determine if a pixel should be added to the list of possible centers.

If there is another pixel to be processed ("YES" branch of decision block 314), then the process repeats for the next pixel at block 266. Otherwise, if all of the pixels in the image have been processed ("NO" branch of decision block 314), then a check is made to determine if there are less than two possible centers. If there are less than two possible centers ("YES" branch of decision block 316), then the threshold limit is decremented by 3 in block 318. If the threshold limit is not less than five ("NO" branch of decision block 320), then the process is repeated for each pixel starting with the first pixel in block 322. Otherwise, if the there are two or more possible centers ("NO" branch of decision block 316) or if the threshold limit is less than five ("YES" branch of decision block 320) then the process returns the list of possible centers to block 224 of flowchart 220 in FIG. 15 at block 324.

Figure 15:
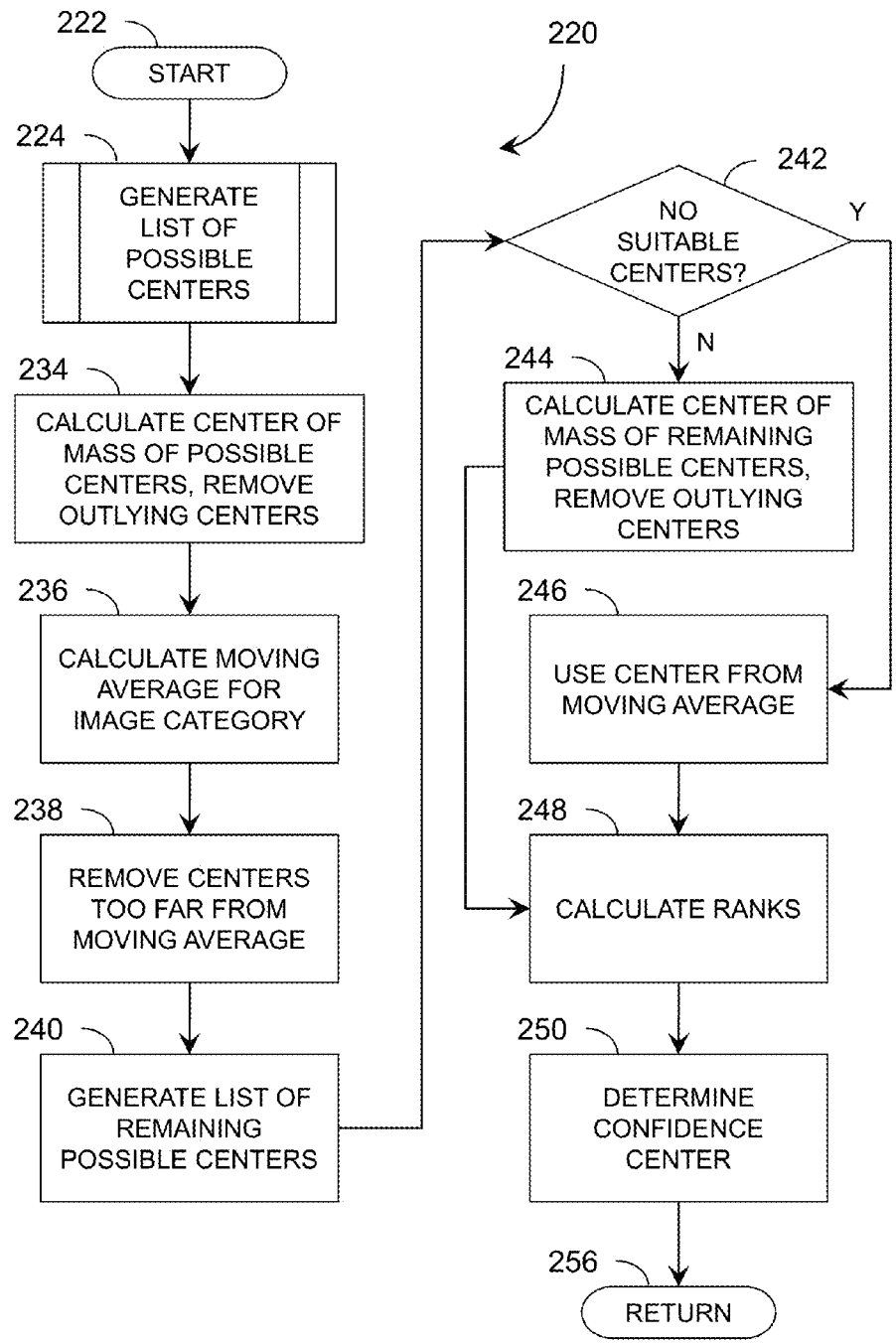
FIG. 15 is a flowchart illustrating a portion of the center detection portion of the image detection algorithm.

Some of the information above used to locate the list of possible centers may also be used in the ranking process at block 248 of flowchart 220 in FIG. 15 in some embodiments. For example, the information relating row totals and/or row state differences may be utilized in the ranking process. A location having fewer differences based on this information may be ranked as "more likely" to be a center of the "C" than a location that has a greater number of differences. Column information or other row attributes may also be used to determine a "more likely" or "less likely" ranking in other embodiments.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art, such as using the image detection algorithm with other detection algorithms or incorporating the image detection algorithm with other evaluation algorithms. The invention in its broader aspects is therefore not limited to the specific details, representative apparatus and method, and illustrative examples shown and described. Accordingly, departures may be made from such details without departing from the scope of the general inventive concept.

What is claimed is:

1. A method of determining an orientation of a Landold C in an image containing a plurality of pixels, the method comprising:
    determining a center of the Landolt C;
    extending a plurality of rays from the center of the Landolt C radially outward;
    determining a plurality of distances, where each distance of the plurality of distances represents a distance from the center of the Landolt C to a darkest pixel along each ray of the plurality of rays;
    identifying a peak in the plurality of distances; and
    determining the orientation of the Landolt C based on the peak in the plurality of distances.

2. The method of claim 1, further comprising:
    calculating a first derivative of the plurality of distances; and
    identifying a peak in the first derivative of the plurality of distances.

3. The method of claim 2, further comprising:
    calculating a second derivative of the plurality of distances; and
    identifying a peak in the second derivative of the plurality of distances.

4. The method of claim 3, wherein determining the orientation of the Landolt C comprises:
    finding at least one a sharp peak in one of the plurality of distances, the first derivative of the plurality of distances, and the second derivative of the plurality of distances;
    in response to finding multiple sharp peaks, following pixels in each of four directions to locate a furthest dark pixel;
    in response to not finding a sharp peak, finding the highest peak in one of the plurality of distances, the first derivative of the plurality of distances, and the second derivative of the plurality of distances; and
    setting the orientation of the Landolt C to a direction corresponding to the sharp peak, the furthest dark pixel, or the highest peak.

5. The method of claim 1, wherein determining the center of the Landolt C comprises using a human observer to select a pixel of the plurality of pixels representing the center of the Landolt C.

6. The method of claim 1, wherein the pixels of the image are organized in rows and columns and determining the center of the Landolt C comprises:
    determining an approximate center of the Landolt C;
    binarizing a plurality of pixels within an area defined by a radius surrounding the approximate center, wherein each binarized pixel of the plurality of pixels is changed to one of black or white;
    determining leftmost and right most columns of binarized pixels containing a black pixel;
    determining uppermost and lowermost rows of binarized pixels containing a black pixel; and
    determining the center of the Landolt C from the determined rows and columns.

7. The method of claim 6, wherein determining the approximate center of the Landolt C comprises:
    generating a list of possible centers;
    calculating a center of mass from the list of possible centers;
    calculating a moving average for the image;
    removing outlying centers based on the center of mass and moving average;
    ranking remaining centers in the list of possible centers;
    returning the center of the list of possible centers with a highest rank as the approximate center; and
    in response to the list of possible centers having no remaining centers, using the moving average as the approximate center.

8. The method of claim 7, wherein the moving average for the image is calculated based on a category of the image.

9. The method of claim 8, wherein the category of the image includes an infrared sensor image, a near infrared sensor image, or a visual sensor image.

10. The method of claim 7, wherein generating the list of possible centers comprises, for each pixel in the plurality of pixels:
    generating a plurality of rays from the pixel to an edge of a circle;
    determining a minimum and a maximum pixel value along each ray of the plurality of rays;
    comparing the difference between the minimum and maximum pixel values to a threshold value for each ray of the plurality of rays;
    in response to the difference being less than the threshold, setting all points along the ray of the plurality of rays to white;
    in response to the difference not being less than the threshold, setting points along the ray of the plurality of rays that exceed the threshold to white and setting remaining points along the ray of the plurality of rays to black;
arranging point values from the plurality of rays in a table;
analyzing attributes of the point values in the table; and
in response to the attributes of the point values in the table meeting established criteria, adding the pixel to the list of possible centers.

11. The method of claim 10, wherein the attributes are selected from a group consisting of: a percentage of white pixels in a column, a total of unchanged pixels in a row, a difference between states of adjacent rows, and combinations thereof.

12. The method of claim 10, wherein the circle has a radius of about 15 pixels.

13. An apparatus comprising:
a processor; and
program code configured to be executed by the processor to determine an orientation of a Landold C in an image containing a plurality of pixels, the program code further configured to determine a center of the Landolt C, extend a plurality of rays from the center of the Landolt C radially outward, determine a plurality of distances, where each distance of the plurality of distances represents a distance from the center of the Landolt C to a darkest pixel along each ray of the plurality of rays, identify a peak in the plurality of distances, and determine the orientation of the Landolt C based on the peak in the plurality of distances.

14. The apparatus of claim 13, wherein the program code is further configured to:
calculate a first derivative of the plurality of distances
calculate a second derivative of the plurality of distances; and
identify a peak in either or both of the first derivative and second derivative of the plurality of distances.

15. The apparatus of claim 14, wherein the program code is configured to determine the orientation of the Landolt C by:
finding at least one a sharp peak in one of the plurality of distances, the first derivative of the plurality of distances, and the second derivative of the plurality of distances;
in response to finding multiple sharp peaks, following pixels in each of four directions to locate a furthest dark pixel;
in response to not finding a sharp peak, finding the highest peak in one of the plurality of distances, the first derivative of the plurality of distances, and the second derivative of the plurality of distances; and
setting the orientation of the Landolt C to a direction corresponding to the sharp peak, the furthest dark pixel, or the highest peak.

16. The apparatus of claim 13, wherein the program code is configured to determine the center of the Landolt C by using a human observer to select a pixel of the plurality of pixels representing the center of the Landolt C.

17. The apparatus of claim 13, wherein the pixels of the image are organized in rows and columns and the program code is configured to determine the center of the Landolt C by:
determining an approximate center of the Landolt C;
binarizing a plurality of pixels within an area defined by a radius surrounding the approximate center, wherein each binarized pixel of the plurality of pixels is changed to one of black or white;
determining leftmost and right most columns of binarized pixels containing a black pixel;
determining uppermost and lowermost rows of binarized pixels containing a black pixel; and
determining the center of the Landolt C from the determined rows and columns.

18. A program product, comprising:
a non-transitory computer recordable type medium; and
a program code configured to determine an orientation of a Landold C in an image containing a plurality of pixels, the program code resident on the non-transitory computer recordable type medium and further configured, when executed on a hardware implemented processor to determine a center of the Landolt C, extend a plurality of rays from the center of the Landolt C radially outward, determine a plurality of distances, where each distance of the plurality of distances represents a distance from the center of the Landolt C to a darkest pixel along each ray of the plurality of rays, identify a peak in the plurality of distances, and determine the orientation of the Landolt C based on the peak in the plurality of distances.

19. The program product of claim 18, wherein the program code is configured to determine the center of the Landolt C by using a human observer to select a pixel of the plurality of pixels representing the center of the Landolt C.

20. The program product of claim 18, wherein the program code is configured to determine the center of the Landolt C by:
determining an approximate center of the Landolt C;
binarizing a plurality of pixels within an area defined by a radius surrounding the approximate center, wherein each binarized pixel of the plurality of pixels is changed to one of black or white;
determining leftmost and right most columns of binarized pixels containing a black pixel;
determining uppermost and lowermost rows of binarized pixels containing a black pixel; and
determining the center of the Landolt C from the determined rows and columns.

* * * * *